United States Patent [19]
Fujimoto et al.

[11] Patent Number: 5,465,625
[45] Date of Patent: Nov. 14, 1995

[54] HEAT MEASUREMENT APPARATUS FOR INSPECTING THERAPEUTIC ENERGY WAVES

[75] Inventors: Katsuhiko Fujimoto, Kanagawa; Satoshi Aida, Tokyo; Masamichi Oyanagi; Nobuki Kudo, both of Tochigi, all of Japan

[73] Assignee: Kabushiki Kaisha Toshiba, Kawasaki, Japan

[21] Appl. No.: 280,546

[22] Filed: Jul. 26, 1994

Related U.S. Application Data

[62] Division of Ser. No. 868,657, Apr. 15, 1992, Pat. No. 5,357,805.

[30] Foreign Application Priority Data

Apr. 15, 1991 [JP] Japan .................................. 3-111045
Mar. 13, 1992 [JP] Japan .................................. 4-055961

[51] Int. Cl.$^6$ .................................. G01L 7/00; G01K 1/08
[52] U.S. Cl. .................................. 73/700; 374/143
[58] Field of Search .................................. 73/700, 708, 714, 73/715, 147; 374/1, 29, 30, 100, 135, 137, 143

[56] References Cited

U.S. PATENT DOCUMENTS

| | | | |
|---|---|---|---|
| 3,832,669 | 8/1974 | Mueller | 338/28 |
| 4,722,609 | 2/1988 | Epstein et al. | 374/30 |
| 4,774,835 | 10/1988 | Holmes et al. | 73/147 |
| 4,812,050 | 3/1989 | Epstein et al. | 374/29 |

*Primary Examiner*—Richard Chilcot
*Assistant Examiner*—William L. Oen
*Attorney, Agent, or Firm*—Oblon, Spivak, McClelland, Maier & Neustadt

[57] ABSTRACT

This invention relates to a heat measurement apparatus for inspecting therapeutic energy waves, e.g. shock waves or ultrasonic waves. The heat measurement apparatus for inspecting focal position and pressure of therapeutic energy waves comprises a heat sensing sheet which changes visually or electrically according to the heat, and a marker for setting the focal position, mounted on the heat sensing sheet.

13 Claims, 7 Drawing Sheets

HEAT MEASUREMENT APPARATUS FOR INSPECTING THERAPEUTIC ENERGY WAVES

CONTINUING DATA

This application is a Divisional of Ser. No. 07/868,657, filed Apr. 15, 1992, now U.S. Pat. No. 5,357,805.

FIELD OF THE INVENTION

This invention relates to a pressure measurement apparatus for inspecting therapeutic energy waves, especially for inspecting the pressure profile at the focal area and the deviation of the focal point from an actual focal position in a treatment apparatus for using shock wave or ultrasound.

DESCRIPTION OF THE PRIOR ART

Recently, in the field of medical treatments, shock wave treatment apparatus has been used, e.g. a lithotripter for disintegrating calculi in a body. Also, an ultrasonic treatment apparatus has been used for heating and treating a cancer in a body. In these treatment apparatus, shock waves or ultrasonic waves, which are released from an applicator which consists of concave shaped piezo-ceramics and a water bag containing coupling fluid, are focused to a focal point In a patient's body. The applicator is set so that the focal point of the energy is coincident with a target e.g. a stone or a cancer. However there are no simple methods to determine whether the apparatus is used at a proper state in which shock waves or ultrasonic waves are irradiated to the target correctly. Therefore, it might happen that medical treatments using these apparatus are not safe and effective.

For example, in a lithotripter using shock waves, a sufficient effect of disintegrating calculi (for example, kidney stones) is not obtained when the focal pressure has been reduced. Moreover, if doctors used the apparatus in which the actual focal position of the shock wave deviates from a focal position marker which is displayed on X-ray images or ultrasonic images, the surrounding tissue would be harmed. Further, if the apparatus was used for long time in unusual state, the life time of the apparatus may be reduced.

Therefore, it is necessary for the user to periodically check the focal position and the pressure profile of the focus.

To measure the pressure profile of focal area in medical treatment apparatus using shock wave, a pressure transducer, e.g. membrane type or a needle type hydrophone is used. Both the membrane type and the needle type hydrophone are discussed in detail in "SHOCK WAVE SENSORS: I. REQUIREMENTS AND DESIGN. Journal of Lithotripsy and Stone Disease Vol.3, No.1, 1991". In the membrane type hydrophone which consists of electrodes which are arranged in two dimensions on a membrane type piezo-electric film, a pressure profile was decided by exposing only once. However, it was difficult to detect the pressure sensing point of the membrane type hydrophone using an ultrasound or an X-ray imaging apparatus because a pressure sensing point of that hydrophone can't be invisible for those imaging apparatus. In short, it is difficult for the user to know the deviation between the actual focal position of the applicator and the imaging focal position.

On the other hand, in the needle type hydrophone (e.g. IMOTEC Corp.'s piezo-electric mini pressure pickup: Type 80-0.5-40), it is easy to detect the sensor position using ultrasound and X-ray imaging apparatus. However, the needle type-hydrophone is broken easily, so that the number of shock wave measurements is restricted. As a result, the needle hydrophone cannot detect the pressure profile of the focal area because the profile detection requires many measurement points. Therefore, it is difficult to detect the deviation between the actual focal position of the applicator and the imaging focal position using the needle type hydrophone.

As mentioned above, in the prior art, the pressure measurement apparatus for inspecting shock waves has both merits and demerits. If the actual focal position of the applicator coincides with the focal position on the image display for a target, the pressure of focal position is measured exactly using a hydrophone. But if the actual focal position of the applicator deviates from the focal position on the image display, the pressure measurement of the direction and the distance of the deviation between the actual focal position of the applicator and the focal position on the image display is very complicated. Thus, it is difficult for the user to determine the focal position.

SUMMARY OF THE INVENTION

It is an object of the present invention to provide a pressure measurement apparatus for inspecting therapeutic energy waves, which makes it easy for user to determine the focal position.

The pressure measurement apparatus for inspecting therapeutic energy waves comprises a pressure sensing sheet which changes visually or electrically according to the pressure of the energy waves and a marker for being set to the focal position on display imaging, which is mounted on the pressure sensing sheet.

The pressure measurement apparatus for inspecting therapeutic energy waves further comprises a mount for holding the pressure sensing sheet in a flat shape, a mount holder for holding the mount, a marker for being set to the focal position held above the pressure sensing sheet, and a holder means for holding the mount holder in a water tank.

DETAILED DESCRIPTION OF THE INVENTION

An embodiment of the present invention will be described hereinafter with reference to the accompanying drawings.

Figure 1:
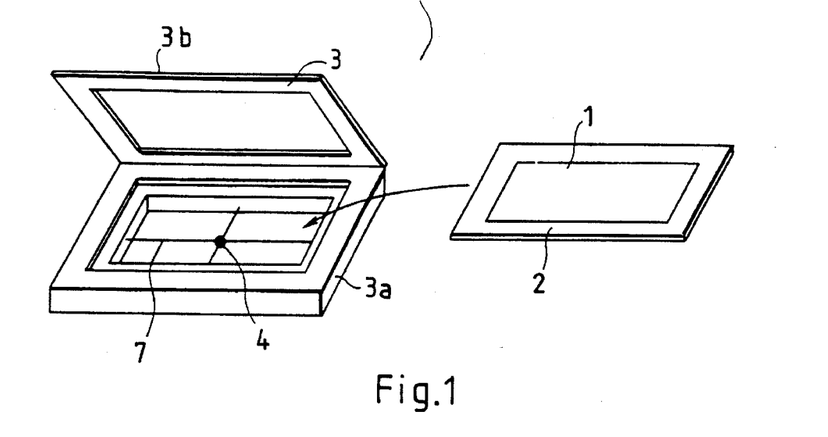
FIG. 1 shows a pressure measurement apparatus according to an embodiment of the present invention.

The pressure measurement apparatus in FIG. 1 comprises a pressure sensing sheet 1, a mount for pressure sensing sheet 2, a mount holder 3 and a marker 4. The pressure sensing sheet 1 consists of a pressure sensing paper 5 whose color is changed partially by additional pressure thereon, and a transparent sticky tape for water-proofing. The pressure sensing paper 5 is e.g. FUJI FILM Corp.-made prescales and 0.045 by 0.04 m.

The mount for pressure sensing sheet 2 has a similar structure to a mount for slides which is marketed. The mount for pressure sensing sheet 2 retains the pressure sensing sheet 1 in a flat shape. The pressure sensing sheet 1 is exchanged for recycling. Further, the mount for pressure sensing sheet 2 may be a disposable type which retains the pressure sensing sheet 1.

The mount holder 3 holds the mount for pressure sensing sheet 2. The mount holder 3 consists of box portion 3a which is a flat shape and a cap portion 3b. The box portion 3a has a step for retaining the mount for pressure sensing sheet 2. The mount for pressure sensing sheet 2 is clipped by the box portion 3a and the cap portion 3b. The marker 4 is used to set a position of ultrasonic and/or X-rays. The marker 4 is a small radio-opaque, which is e.g. glass, titanium (Ti), Iron (Fe), tin (Sn), tungsten (W) and tantalum(Ta). The marker 4 is retained at the center of the open side of the mount holder 3 by wire 7, which has nearly the acoustic impedance of water and is radio-lucent, e.g. rubber, glass, silicon (Si) and polyester. In this case, the marker 4 is held above the pressure sensing sheet 1. If the marker 4 contacts the pressure sensing sheet 1, when the shock wave exposes the pressure sensing sheet 1, a reflection could cause contact between the pressure sensing sheet 1 and the marker 4. As a result, it is impossible to exactly measure the focal pressure.

When the pressure of a shock wave is measured by using the pressure measurement apparatus, the pressure measurement apparatus is held in a water tank by a holder. The pressure measurement apparatus is exposed to the shock wave by the shock wave source 23, which is an applicator of a water bag type.

Figure 3:
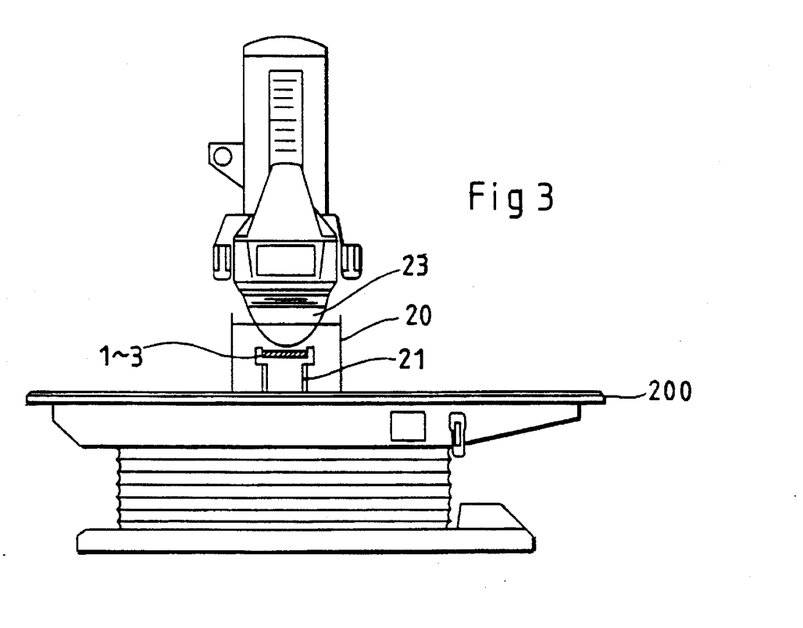
FIG. 3 is a side figure showing the pressure measurement apparatus, which is used in a shock wave treatment apparatus according to the embodiment of the invention.

FIG. 3 shows the pressure measurement apparatus of the present invention which is established in the shock wave treatment apparatus. As shown in the FIG. 3, the pressure sensing sheet 1, the mount 2 and the mount holder 3 are mounted in the water tank 20 by holder 21. When the pressure measurement apparatus measures the focal position of the shock wave source 23, the pressure measurement apparatus must be in a set position.

FIG. 4 relates the focal position marker 50 on the image display 60, which is used to set the focal position of the lithotripter and color emitting state. FIG. 4A and 4B show that the actual focal position of shock wave (i.e. spot 80) coincides with the focal position marker 50 on image display 60 FIG. 4B shows the relative position of the focal position of the shock wave in the pressure sensing sheet 1 and marker 4. Further, the position is set by using X-rays, because the marker 4 is radio-opaque.

Figure 4A:
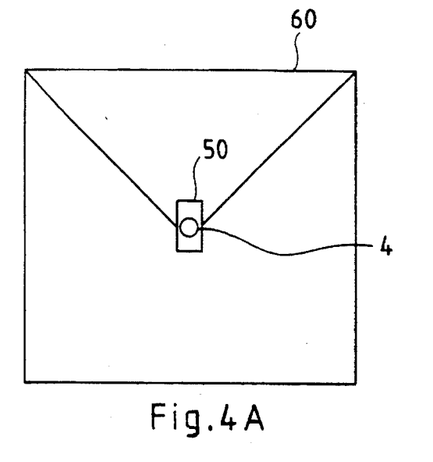
FIG. 4A, 4B, 4C and 4D shows the relationship between the focal position marker on an image display and a color emitting state.
Figure 4B:
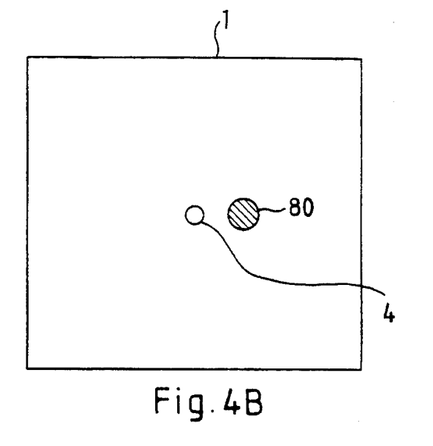
Figure 4C:
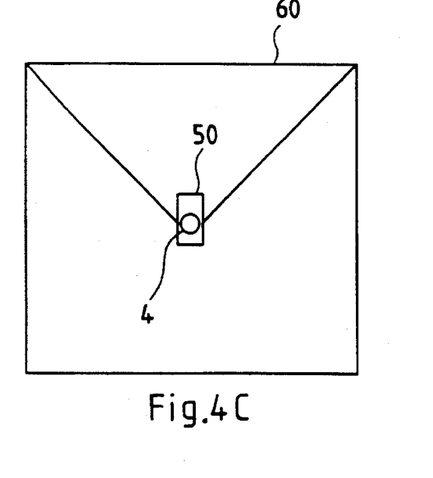
Figure 4D:
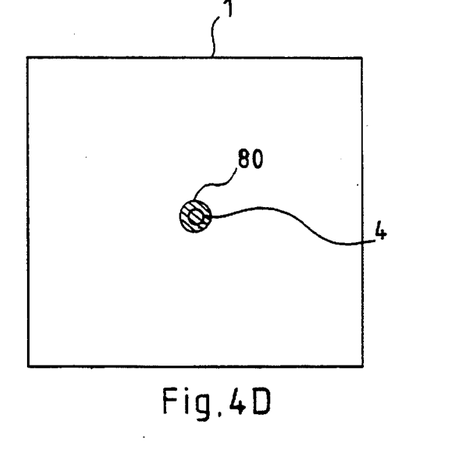

The position is set as the marker 4 coincides with the focal position marker 50. But actually, the spot 80 deviates from the marker 4. After the position is set according to distance and direction between the marker 4 and the spot 80 on the pressure sensing sheet 1, the shock wave source 23 is operated. In this way, the user sets the focal position by referring to the deviation of the spot 80 on the pressure sensing sheet 1. Finally, as shown in FIG. 4C and 4D, spot 80 coincides with the focal position marker 50 and the marker 4.

As mentioned above, FIG. 4 shows the set position of the marker 4 which is coincident with the focal position marker 50 on the image display 60. Also, this invention operates to adjust the focus pressure to the most suitable pressure. Concretely speaking, when the maximum pressure of the focal position, which is guaranteed by the shock wave treatment apparatus, comes down 0%, 10%, 20% and 30% respectively, each color emitting state is recorded as a standard color emitting state.

Figure 5A:
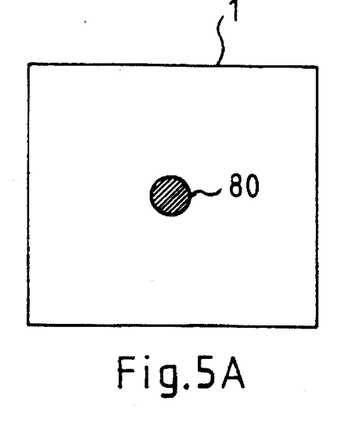
FIG. 5A, 5B, 5C and 5D illustrate how the color changes when the shock wave has less energy.
Figure 5B:
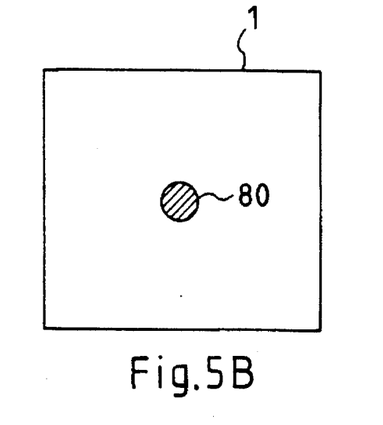
Figure 5C:
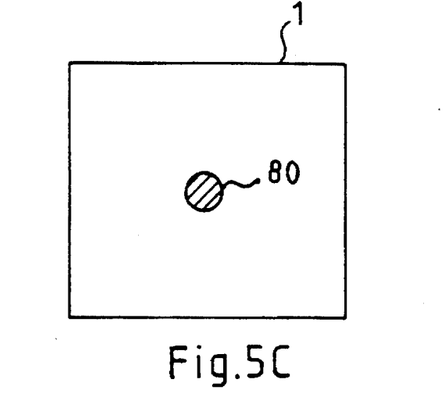
Figure 5D:
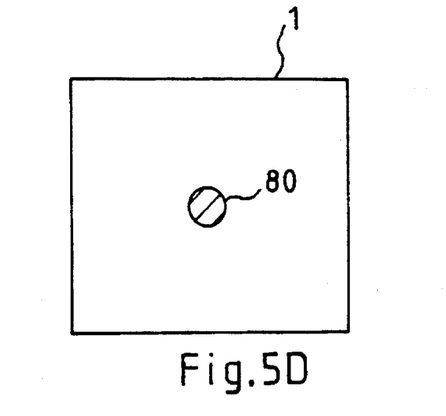
Figure 6A:
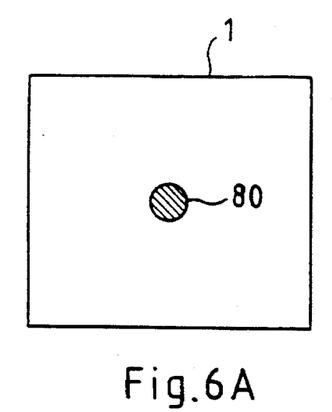
FIG. 6A–D illustrate how the size of the color changes when the shock wave has less energy.
Figure 6B:
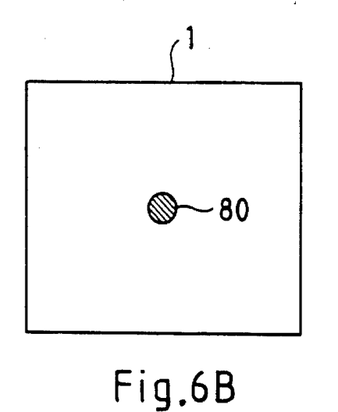
Figure 6C:
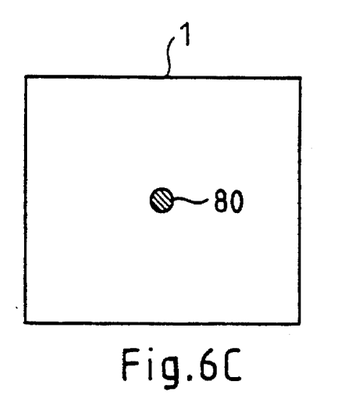
Figure 6D:
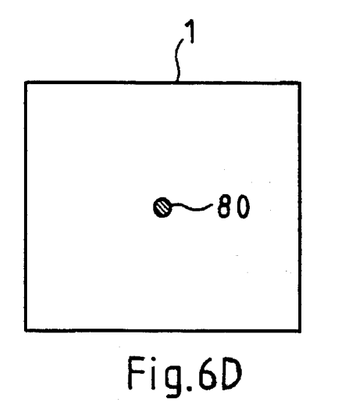

FIG. 5A and 6A show the color emitting state of the pressure sensing sheet 1, when the maximum pressure of the focal position comes down. FIG. 5B shows the color emitting state when the pressure value comes down 10% from the maximum pressure. FIG. 5C shows the color emitting state when the pressure value comes down 20% from the maximum. FIG. 5D shows the color emitting state when the pressure value comes down 30% from the maximum. FIG. 6 is different from the FIG. 5, in that FIG. 5 shows that when the maximum pressure comes down the color is more light, but in FIG. 6, when the maximum pressure comes down, the color area is smaller. Thus, the user compares the actual color emitting area with a standard color emitting which is previously recorded as the maximum pressure, when the shock wave treatment apparatus is inspected by the user. The user can judge how much the pressure has come down. As a result, the user can decide whether the actual maximum pressure is enough, and whether a serviceman must examine the shock wave treatment apparatus.

Figure 7:
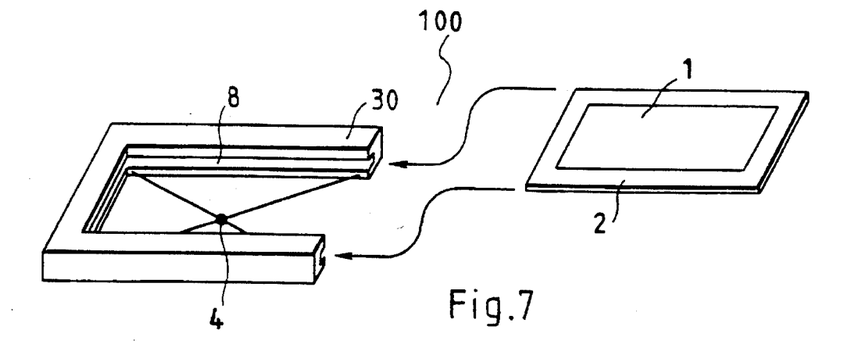
FIG. 7 shows a pressure measurement apparatus according to another embodiment of the invention.

FIG. 7 shows another embodiment of the pressure measure apparatus according to the present invention, which is different from the mount holder 3 of the FIG. 1. The mount holder 3 consists of a frame, which has an opening side and has gutter 8 to insert the mount of the pressure sensing sheet 2 from the opening side, as shown by the pointing arrow in FIG. 7.

Figure 2:
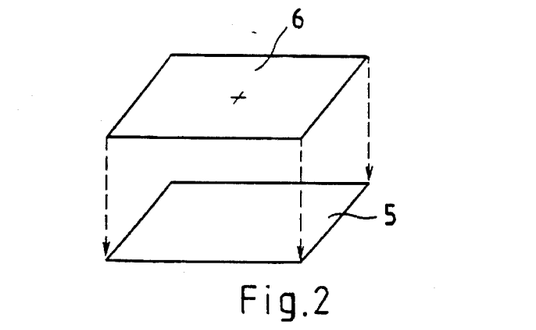
FIG. 2 shows a pressure sensing sheet shown in FIG. 1.
Figure 8:
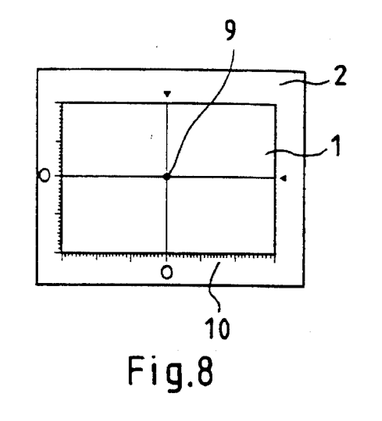
FIG. 8 shows a mount for a pressure sensing sheet shown in FIG. 1.
Figure 9:
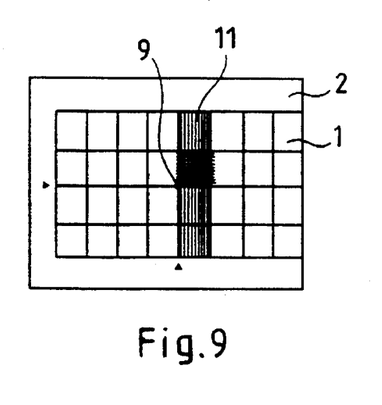
FIG. 9 shows another mount for a pressure sensing sheet shown in FIG. 7.

FIG. 8 and 9 show other embodiments of the pressure sensing sheet 1 and the mount for pressure sensing sheet 2. As shown in FIG. 8, an indication mark for focal position 9 has a different color (e.g. blue, if the color of the pressure sensing paper 5 is red) from the color of the pressure sensing paper 5. The indication marker 9 is marked on the surface of transparent tape 6, which contacts the pressure sensing sheet 1, as shown FIG. 2, and the marker 4. The indication mark for focal position 9 is e.g. a dot, a cross, or two straight lines, and the cross point indicates the focal position.

In this case, the mount for pressure sensing sheet 2 has scale 10, which has a zero point corresponding to the focal position for focal position 9. As a result, deviation of actual focal position and geometric focal position may be measured quantitatively.

As shown in FIG. 9, cross hair 11 is printed on the pressure sensing sheet 1. The zero point of the cross hair 11 is the focal position of the indication mark 9. In these ways, the effect of this embodiment is the same as that of FIG. 8.

FIGS. 10–14 show the embodiment in which the pressure measurement apparatus of the present invention is actually applied to the shock wave treatment apparatus.

Figure 10:
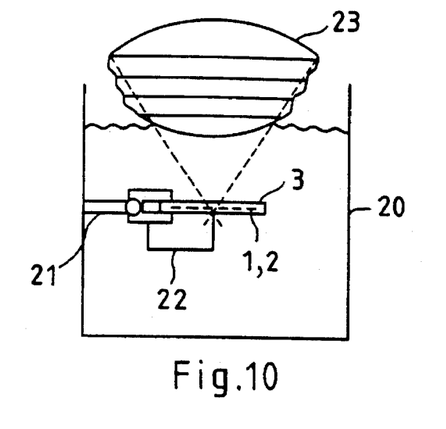
FIG. 10 shows an arrangement for the pressure sensing sheet shown in FIG. 1.

As shown in FIG. 10, the pressure measurement apparatus is established horizontally and the pressure sensing sheet is established perpendicular to the focus direction of the shock wave by holder 21 in the water tank 20. The point of the shock wave source 23 is dipped in the water bag and the pressure measurement apparatus measures the focal position pressure for the shock wave irradiated from the shock wave source 23. In this case, the water tank 20 or the holder 21, which is on the marker, may be used.

Figure 11:
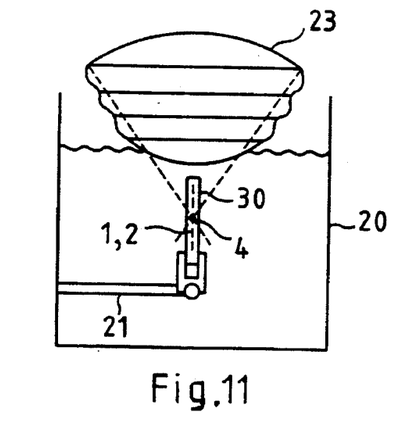
FIG. 11 shows another arrangement for the pressure sensing sheet shown in FIG. 9.

FIG. 11 shows another embodiment different from FIG. 10. The pressure measurement apparatus is established vertically, in other word, parallel to the focus direction of the shock wave.

In this case, the mount for pressure sensing sheet 2, whose one side is removed as shown in FIG. 9, is adopted and the mount holder 3, whose one side is removed. As shown in FIG. 7, the pressure sensing sheet 1 is set parallel to the focus direction of shock wave and the pressure measurement apparatus can measure the pressure distribution in the focus direction of the shock wave.

Figure 12:
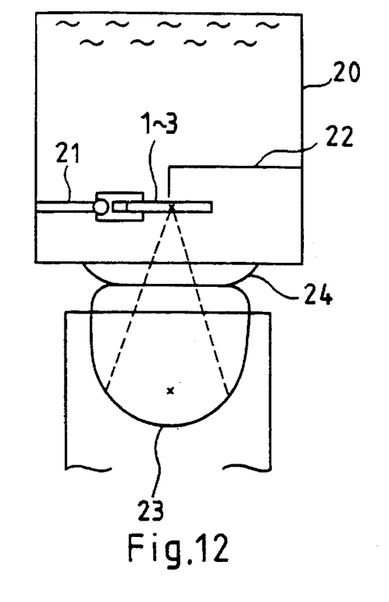
FIG. 12 shows an arrangement for the pressure measurement apparatus according to the base contact shock wave source.

FIG. 12 shows another embodiment wherein shock wave source 23 contacts a membrane 24, which is established on the base of the water tank 20.

Figure 13:
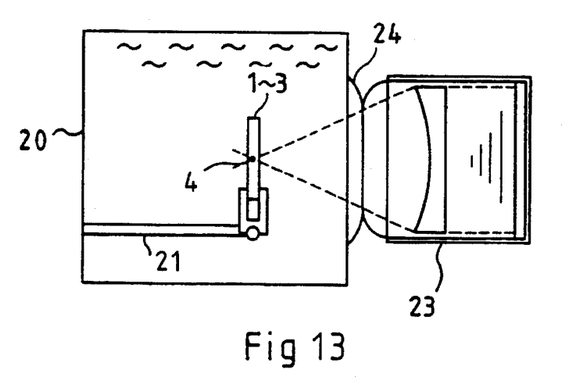
FIG. 13 shows another arrangement for the pressure measurement apparatus according to the base contact shock wave source.

FIG. 13 shows another embodiment wherein shock wave source 23 contacts a membrane 24, which is established on the side of the water tank 20.

Figure 14:
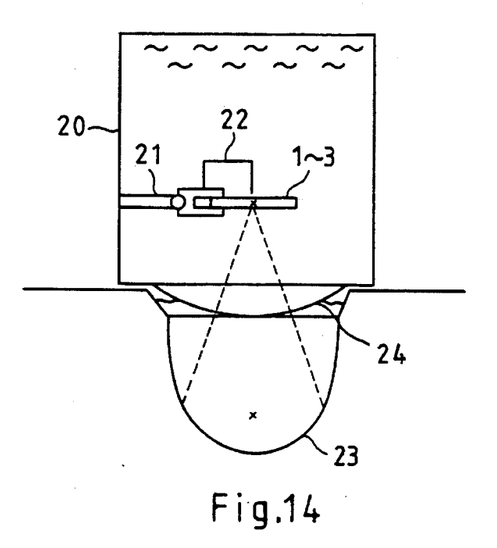
FIG. 14 shows an arrangement for the pressure measurement apparatus using an open type lithotripter which has a base contact shock wave source.

FIG. 14 shows another embodiment applied to an open type lithotripter. This case, which is similar to FIG. 12, shows the shock wave source 23 contacting a membrane 24, which is established on the base of the water tank 20.

The embodiments in FIG. 11 and FIG. 13 show the small ball as the marker 4. But in the embodiments shown in FIG. 10, 12 and 14, in which the pressure measurement apparatus is established horizontally, it is possible to hold needle type marker 22 to the water tank 20 or holder 21 without contacting the pressure sensing sheet 1.

Figure 15:
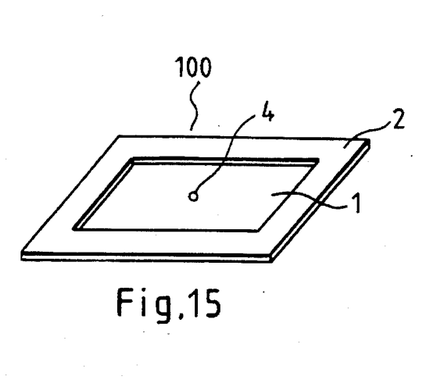
FIG. 15 shows an arrangement for a marker according to an embodiment of the present invention.

In the above embodiments, the marker 4(22) was established at the back of the pressure sensing sheet 1, which is opposite to the side of the shock wave source. But as for the lithotripter which is an ultrasonic portrait type, the ultrasonic is reflected in front of the pressure sensing sheet 1. Thus, it often happens that the marker 4 at the back of the pressure sensing sheet 1 is not visible. In this case, to confirm position setting accuracy, the marker 4 is established in front of the pressure sensing sheet 1. In this method, the marker 4 is held on the surface of the pressure sensing sheet 1 by an adhesive agent, as shown in FIG. 15.

However, if the marker 4 is established in front of the pressure sensing sheet 1, pressure distribution on the surface of the pressure sensing sheet 1 is confused. Therefore, the accuracy of pressure measurement value is reduced. Thus, as shown in FIG. 8 and FIG. 9, a pressure sensing sheet 1 which has a mark for focal position 9 indicated on the pressure sensing paper 5, is adopted. The marker 4 is fixed at the center of the front of the pressure sensing sheet 1. The user then sets the focal position for the lithotripter according to the marker 4. When strong ultrasonic for treatment is used, the marker 4 is removed from the pressure sensing sheet 1. Such being the case, confusion of pressure distribution on the front surface of the pressure sensing sheet 1 disappears and it is possible to set the focal position and measure the pressure value exactly.

Figure 16:
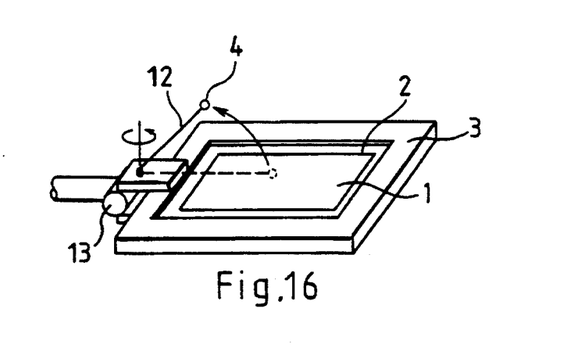
FIG. 16 shows another arrangement for an marker according to an embodiment of the present invention.

FIG. 16 shows the embodiment of the pressure measurement apparatus, which is applied to this method. The pressure measurement apparatus prepares the marker 4, which is mounted on top of thin arm 12 and the arm 12 is mounted on driving mechanism 13, which can rotate. If the arm 12 is rotated by the driving mechanism 13, the marker 4 is set in front of the pressure sensing sheet 1 and is detached from front of the pressure sensing sheet 1.

Figure 17A:
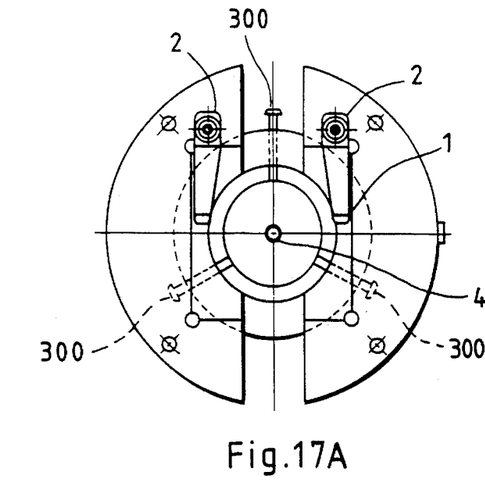
FIG. 17A shows an arrangement for a marker according to another embodiment of the invention.
Figure 17B:
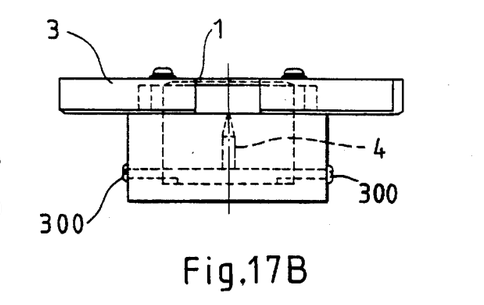
FIG. 17B shows an arrangement for a marker according to another embodiment of the invention.

Moreover, FIG. 17 shows another embodiment in that the marker 4, which is a needle type, contacts the back of the pressure sensing sheet 1. FIG. 17A shows a diagram on the top view of the pressure measurement apparatus in this embodiment FIG. 17B shows a diagram on the side view of the pressure measurement apparatus in this embodiment. In this case, the pressure measurement apparatus is established in a water bag and the focal position of the shock wave source is set so that the focal position coincides with the focal position marker (NOT shown) in the ultrasonic portrait. In this state, if the shock wave is exposed, a color emitting point corresponding to the pressure of the shock wave appears on the pressure sensing sheet 1.

Then an object (an innerprove) is pushed against the pressure sensing sheet 1, which contacts the marker 4. As a result, a point, between the innerprove and the marker 4 appears as strong color emitting point. Thus, if the interval between two color emitting points on the pressure sensing sheet 1 is measured, the deviation between the focal point of the shock wave source and the marker 4 is detected exactly. Further, the deviation is detected by holding up the pressure sensing sheet 1 to light. It is also detected by lighting from the opposite surface of the pressure sensing sheet 1.

Figure 18:
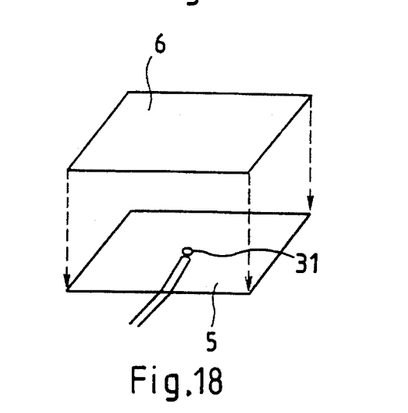
FIG. 18 shows another pressure sensing sheet for applying a pressure transducer.
Figure 19:
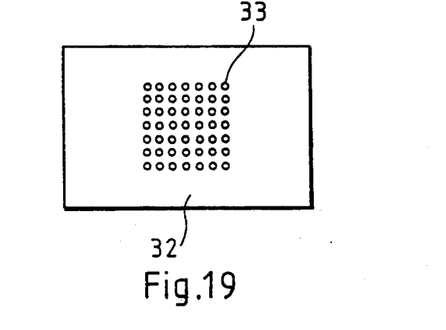
FIG. 19 shows yet another pressure sensing sheet for applying a membrane type piezoelectric film.

Next, FIGS. 18 and 19 show the other embodiment of the pressure sensing sheet. As shown in FIG. 18, the pressure transducer 31, which is a small membrane type, is held by the transparent sticky tape for water-proofing 6 on the pressure sensing paper 5. Using this system, even if the focal position corresponding to the marker 4 and focal position corresponding to the shock wave are different, the deviation of detection and quantity is detected easily. Accordingly, the user can revise the deviation. After that, by emitting the shock wave, the pressure measurement apparatus can measure the focal position pressure exactly.

FIG. 19 shows a pressure sensing sheet which is a hydrophone consisting of electrodes 33 arranged by the same interval on a membrane type piezo-electric film 32. In the pressure sensing sheet, when the shock wave is irradiated to the film 32, an electric signal, which has a different level corresponding to the pressure distribution of the shock wave, is gained from the electrode as the output of the hydrophone. Therefore, according to the output of the hydrophone, the sound field, or peak pressure in the focal position, still more deviation between the focal position corresponding to the relative position of the applicator and the actual focal position, are measured. As for the value of these measurements which result, the user can understand whether the output will break the calculus, can judge if the treatment apparatus is operating properly, and can detect any unusual output easily.

The pressure sensing sheet has pressure a sensible extent of e.g. 50–100 Mpa. But it often happens that the shock wave irradiated by lithotripter is not within the pressure sensible extent.

For example, when the maximum output of the shock wave is 1200 Mpa, even if the maximum output of the shock wave goes down 20%, the pressure sensing sheet can't detect the change. Conversely, when the maximum output of the shock wave is 40 Mpa, the pressure sensing sheet will not detect this level, so that it is impossible to measure. In this case, pressure sensing sheets shown in FIG. 20 or 21, are suitable.

Figure 20:
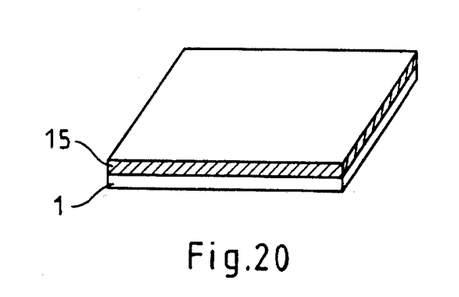
FIG. 20 shows a pressure sensing sheet on which a damping film is used.

FIG. 20 shows pressure sensing sheet for high-pressure. In FIG. 20, on the front surface of the pressure sensing sheet 1, a damping film 15, e.g. a rubber sheet, is adhered. The space between the damping film 15 and the pressure sensing sheet 1 is a vacuum. If the pressure sensing sheet is used in the same manner in the earlier described embodiment, the transparency output of shock wave decreases by 20%, so the pressure sensing sheet can detect the maximum output of 120 Mpa of the lithotripter. Further, by choosing the acoustic characteristics, a suitable damping quantity is set up for the damping film 15.

Figure 21:
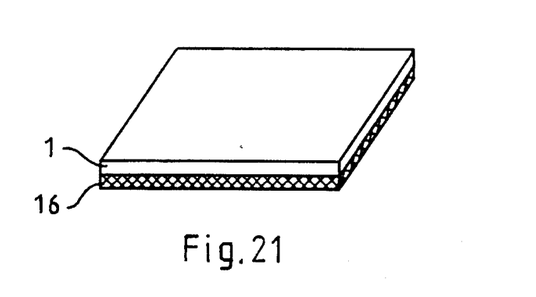
FIG. 21 shows a pressure sensing sheet on which a reflecting film is used.

FIG. 21 shows a pressure sensing sheet for low-pressure. In FIG. 21, on the back surface of the pressure sensing sheet 1, a reflection film 16 which has an acoustic impedance more than that of the sensing sheet 1, e.g. stainless, is adhered. The space between the reflection film 16 and the pressure sensing sheet 1 is a vacuum. If the pressure sensing sheet is used in the described embodiments, the output of the shockwave may be increased by 50%, so the pressure sensing sheet may be used for the maximum output of 40 Mpa of the lithotripter.

Further the pressure sensing paper 5 may be exchanged for heat sensing paper. Thus, a heat sensing sheet, when the heat sensing paper is adopted, can apply for inspection of ultrasonic treatment apparatus for hyperthermia.

What is claimed is:

1. A heat measurement apparatus for used therapeutic energy waves, comprising:

means for producing therapeutic energy waves that focus at a focal position;

a heat sensitive sheet of material having first and second opposing edges, visual properties, and electrical properties, wherein at least one of said visual properties and said electrical properties changes when heat is applied to said heat sensitive sheet;

means for mounting said heat sensitive sheet, said means for mounting located adjacent said first and second opposing edges of said heat sensitive sheet;

a marker located on said means for mounting, wherein, when said heat sensitive sheet is mounted on said means for mounting, said marker is adjacent an adjacent region of said heat sensitive sheet and can be used to indicate said adjacent region;

whereby a user may align a region of said heat sensitive sheet at said focal position of said therapeutic energy waves, at which one of said visual properties and said electrical properties of said heat sensitive sheet has been changed, with said adjacent region.

2. An apparatus according to claim 1, further comprising:
   a sheet holding means for holding said heat sensitive sheet flat.

3. An apparatus according to claim 1, further comprising:
   transparent sticky tape on said heat sensitive sheet of material for water-proofing said heat sensitive sheet of material.

4. An apparatus according to claim 1, wherein said marker for setting said focal position is mounted adjacent to a side of said heat sensitive sheet of material that is the second side with respect to the direction of propagation of energy waves from said means for producing therapeutic energy waves.

5. An apparatus according to claim 1, further comprising:
   a marker holding means for holding said marker for setting said focal position above said heat sensitive sheet, said marker holding means being directly connected to said means for mounting.

6. An apparatus according to claim 1, further comprising:
   a marker driving means for driving said marker adjacent to said heat sensitive sheet of material and for removing said marker from adjacent to said heat sensitive sheet of material.

7. An apparatus according to claim 1, wherein:
   said heat sensitive sheet of material includes means to provide an indication for setting a focal position of said therapeutic energy waves when said marker is removed from adjacent to said heat sensitive sheet of material.

8. An apparatus according to claim 1, wherein said means for mounting said marker is located above said heat sensitive sheet of material, and wherein said means for mounting holds said marker at a center of an open space of said means for mounting that is between said heat sensitive sheet of material and said means for producing therapeutic energy waves.

9. An apparatus according to claim 1, wherein said means for mounting comprises:
   a material whose acoustic impedance is similar to water.

10. An apparatus according to claim 1, wherein said means for mounting comprises:
    a material whose acoustic impedance is transparent to x-rays.

11. An apparatus according to claim 1, wherein said marker is a needle-type marker which is mounted on said means for mounting so that a point of said marker contacts the back surface of said heat sensitive sheet of material relative to a direction of propagation of said therapeutic energy waves and said needle type marker is orientated with a long axis perpendicular to the heat sensitive sheet of material.

12. An apparatus according to claim 1, further comprising a heat reflection film which is adhered to a surface of said heat sensitive sheet of material, whereby said heat reflection film increases the heat produced due to said therapeutic energy waves impinging on said heat sensitive sheet material.

13. An apparatus according to claim 1, wherein said means for producing therapeutic energy waves comprises means for producing ultrasonic waves.

\* \* \* \* \*